US00PP14306P39

(12) United States Plant Patent
Yomo

(10) Patent No.: US PP14,306 P3
(45) Date of Patent: Nov. 18, 2003

(54) VERBENA PLANT NAMED 'SUNMARIRO'

(50) Latin Name: *Verbena hybrida*
Varietal Denomination: cv. Sunmariro

(75) Inventor: Yasunori Yomo, Yasu-gun (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 10/066,734

(22) Filed: Feb. 6, 2002

(65) Prior Publication Data

US 2003/0150038 P1 Aug. 7, 2003

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | |
|---|---|---|---|
| PP8,995 | P | 11/1994 | Tachibana et al. |
| PP9,014 | P | 12/1994 | Tachibana et al. |
| PP9,059 | P | 2/1995 | Tachibana et al. |
| PP9,085 | P | 3/1995 | Tachibana et al. |
| PP9,121 | P | 4/1995 | Tachibana et al. |
| PP9,411 | P | 12/1995 | Tachibana et al. |
| PP10,311 | P | 3/1998 | Tachibana |
| PP10,705 | P | 11/1998 | Tachibana |
| PP10,743 | P | 1/1999 | Nagase |
| PP10,755 | P | 1/1999 | Nagase |
| PP10,801 | P | 2/1999 | Nagase |
| PP11,037 | P | 8/1999 | Yomo et al. |
| PP11,104 | P | 10/1999 | Yomo et al. |
| PP11,113 | P | 11/1999 | Yomo et al. |
| PP11,120 | P | 11/1999 | Yomo et al. |
| PP11,130 | P | 11/1999 | Yomo et al. |

*Primary Examiner*—Kent Bell
(74) *Attorney, Agent, or Firm*—Burns, Doane, Swecker & Mathis, L.L.P.

(57) ABSTRACT

Disclosed herein is a new and distinct variety of a broadly spreading Verbena plant. The new Verbena plant has abundant branching particularly with respect to primary branching, and a great profusion of blooms with the entire plant remaining in bloom for a considerable period of time. The flowers are large and the petals display a vivid red color without an eye. The flowers are formed in profusion in a spike. The blooming period is from early April to November, and the flowering duration is long. The plant exhibits high tolerance to cold and heat, high resistance to pests and diseases, particularly powdery mildew, and high resistance to rain.

2 Drawing Sheets

Botanical/commercial classification: *Verbena hybrida*/ Verbena Plant.
Varietal denomination: cv. 'Sunmariro'.

BACKGROUND OF THE VARIETY

The present invention relates to a new and distinct variety of Verbena plant obtained from a crossing of Verbena plant variety *Verbena hybrida* 'H39-2' (non-patented in the United States) and the same *Verbena hybrida* 'H39-2'.

The Verbena is a very popular plant and is used for flower bedding and potting in the summer season. There are only a few varieties of the Verbena plant which have a spreading growth habit, abundant branching, many flowers in a spike, and a high resistance to heat, cold, and diseases. Accordingly, this invention is aimed at obtaining a new variety having a spreading growth habit, much branching, many flowers in a spike, vivid red flowers having a large diameter, high tolerance to heat and cold, and resistance to diseases and pests.

The variety 'H39-2' (non-patented in the United States) was obtained from the open-pollination of the Verbena variety '135-2' and an unknown Verbena plant. Seedlings were obtained in the July of 1997, from crossing 'H39-2' as the female parent and the same Verbena plant, and were grown from the September of 1997 at Kitakoma-gun, Yamanashi-ken, Japan. Among these plants, one was selected in view of its spreading growth habit and petal color, and was propagated by use of cuttings, and then was evaluated beginning in January 1998. The botanical characteristics were examined, using similar 'SUNVP-PI' (U.S. Plant Pat. No. 10,705) for comparison. As a result, it was concluded that this new Verbena variety is distinguishable from any other variety whose existence is known to me and is uniform and stable in its characteristics. This new variety was named 'Sunmariro'.

In the following description, the color-coding is in accordance with The R.H.S. Colour Chart of The Royal Horticultural Society, London, England. A color chart based on The Japan Color Standard for Horticultural Plants (J.H.S. Color Chart) is also added for reference.

The main botanical characteristics of variety 'H39-2' are as follows:

Plant:
- *Growth habit.*—Spreading.
- *Extension.*—Broad (approximately 80–100 cm).
- *Height.*—Medium (approximately 15–20 cm).

Stem:
- *Diameter.*—Medium (approximately 1.5–2.5 mm).
- *Anthocyanin pigmentation.*—Present.
- *Pubescence.*—Medium.
- *Prickles.*—Absent.
- *Branching.*—Abundant.
- *Subterranean stem.*—Absent. But when the stems contact the surface of soil, the nodes commonly take root in the ground and the resulting plant has a spreading growth habit.
*Length of internode.*—Medium (approximately 2.0–4.0 cm).

Leaf:
*Phyllotaxis.*—Opposite.
*Shape of blade.*—Oblong.
*Depth of blade incision.*—Shallow.
*Blade crenation of margin.*—Serrate.
*Length.*—Medium (approximately 3.0–4.5 cm).
*Width.*—Medium (approximately 1.5–2.5 cm).
*Color.*—Grayish olive green (R.H.S. Colour Chart No. 137A, J.H.S. Color Chart No. 3716).
*Pubescence.*—Sparse.
*Petiole.*—Present.
*Diameter of petiole.*—Medium (approximately 1.0–1.2 mm).
*Length of petiole.*—Short (approximately 2.0–2.2 mm).

Flower:
*Shape of cluster.*—Funnel-shaped.
*Length of cluster.*—Medium (approximately 30–50 mm).
*Diameter of cluster.*—Medium (approximately 50–60 mm).
*Facing direction.*—Upward.
*Outward curvature of petal.*—Slightly curved.
*Diameter.*—Large (approximately 1.5–2.0 cm).
*Height.*—High (approximately 2.0–3.0 cm).
*Color.*—Vivid red (R.H.S. Colour Chart No. 45B, J.H.S. Color Chart No. 0407).
*Eye color.*—Absent.
*Variegation on petal.*—Absent.
*Overlapping of petals.*—Separate.
*Incision of petal.*—Present.
*Number of petals.*—Medium.
*Incision of calyx.*—Present.
*Length of calyx.*—Long (approximately 1.0–1.2 cm).
*Anthocyanin pigmentation of calyx limb.*—Present.
*Shape of pistil.*—Two lobes.
*Number of stamens.*—Medium.
*Color of anther.*—Yellow green.
*Diameter of peduncle.*—Thin (approximately 1.0–2.0 mm).
*Length of peduncle.*—Medium (approximately 40–50 mm).
*Number of flowers.*—Medium.
*Reproductive organs.*—1 pistil and 4 stamens.
*Flower fragrance.*—Absent.
*Flowering time.*—Medium.
*Flowering duration.*—Long.

Physiological and ecological characteristics: High resistance to diseases and pests, particularly powdery mildew. High tolerance to heat and drought. High tolerance to rain and to cold.

The 'SUNVP-PI' variety used as a comparison is the subject of U.S. Plant Pat. No. 10,705. The main botanical characteristics of 'SUNVP-PI' are as follows:

Plant:
*Growth habit.*—Spreading.
*Plant extension.*—Broad (approximately 50–70 cm).
*Plant height.*—Medium (approximately 15–25 cm).

Stem:
*Diameter.*—Medium (approximately 2–3 mm).
*Anthocyanin pigmentation.*—Present.
*Pubescence.*—Medium.
*Prickles.*—Absent.
*Branching.*—Medium.
*Subterranean stem.*—Absent.
*Length of internode.*—Medium (approximately 4.0–5.0 cm).

Leaf:
*Phyllotaxis.*—Opposite.
*Shape of blade.*—Hastate.
*Blade of incision.*—Present.
*Depth of brade incision.*—Shallow.
*Crenation of blade margin.*—Serrate.
*Length.*—Medium (approximately 4.0–5.0 cm).
*Width.*—Medium (approximately 2.0–2.5 cm).
*Color.*—Grayish olive green (R.H.S. Colour Chart No. 137A, J.H.S. Color Chart No. 3716).
*Pubescence.*—Medium.
*Petiole.*—Present.
*Petiole diameter.*—Medium (approximately 1.0 mm).
*Petiole length.*—Medium (approximately 2.0 mm).

Flower:
*Shape of cluster.*—Funnel-shaped.
*Cluster length.*—Medium (approximately 3.0–3.5 cm).
*Cluster diameter.*—Medium (approximately 5.0–5.5 cm).
*Facing direction.*—Upward.
*Outward curvature of petal.*—Curved.
*Diameter.*—Large (approximately 1.5–2.0 cm).
*Height.*—Medium (approximately 2.0 cm).
*Color of petal.*—Deep purplish pink (R.H.S. Colour Chart No. 70C, J.H.S. Color Chart No. 9213).
*Eye color.*—Absent.
*Variegation.*—Absent.
*Color intensity.*—Present.
*Overlapping of petals.*—Separate.
*Number of petal.*—Medium (5).
*Calyx incision.*—Absent.
*Calyx length.*—Long (approximately 1.0 cm).
*Anthocyanin pigmentation of calyx limb.*—Present.
*Number of stamens.*—Medium.
*Color of anther.*—Yellow green.
*Peduncle diameter.*—Medium (approximately 2.0–3.0 mm).
*Peduncle length.*—Medium (approximately 5.0–6.0 cm).
*Number of flowers.*—Many (approximately 14–16).
*Reproductive organs.*—1 pistil and 4 stamens.
*Flower fragrance.*—Absent.
*Flowering time.*—Early.
*Flowering duration.*—Long.

Physiological and ecological characteristics:
*Tolerance to cold.*—Medium.
*Tolerance to heat.*—High.
*Resistance to diseases.*—High.
*Resistance to pests.*—High.

The variety 'Sunmariripi' variety used as a comparison is the subject of U.S. Plant Pat. No. 11,037. The main botanical characteristics of the 'Sunmariripi' variety are as follows:

Plant:
*Growth habit.*—Spreading.
*Plant extension.*—Broad (approximately 50–70 cm).
*Plant height.*—Medium (approximately 10–20 cm).

Stem:
*Diameter.*—Medium (approximately 2.0–3.0 mm).

*Anthocyanin pigmentation.*—Present.
*Pubescence.*—Medium.
*Prickles.*—Absent.
*Branching.*—Medium.
*Subterranean stem.*—Absent.
*Length of internode.*—Medium (approximately 2.0–4.0 cm).

Leaf:
*Phyllotaxis.*—Opposite.
*Shape of blade.*—Hastate.
*Blade of incision.*—Present.
*Depth of brade incision.*—Shallow.
*Crenation of blade margin.*—Serrate.
*Length.*—Medium (approximately 2.5–4.5 cm).
*Width.*—Medium (approximately 1.5–2.5 cm).
*Color.*—Grayish olive green (R.H.S. Colour Chart No. 137A, J.H.S. Color Chart No. 3716).
*Pubescence.*—Sparse.
*Petiole.*—Present.
*Petiole diameter.*—Medium.
*Petiole length.*—Short (approximately 2.0–2.2 mm).

Flower:
*Shape of cluster.*—Funnel-shaped.
*Cluster length.*—Medium (approximately 3.0–6.1 cm).
*Cluster diameter.*—Medium (approximately 5.1–5.6 cm).
*Facing direction.*—Upward.
*Outward curvature of petal.*—Slightly curved.
*Diameter.*—Large (approximately 1.5–2.0 cm).
*Height.*—Medium (approximately 1.7–2.0 cm).
*Color of petal.*—Deep purplish pink (R.H.S. Colour Chart No. 55A, J.H.S. Color Chart No. 9705).
*Eye color.*—Present.
*Variegation.*—Absent.
*Color intensity.*—Absent.
*Overlapping of petals.*—Separate.
*Number of petals.*—Medium (5).
*Calyx incision.*—Present.
*Calyx length.*—Long (approximately 1.1–1.3 cm).
*Anthocyanin pigmentation of calyx limb.*—Absent.
*Peduncle diameter.*—Thin (approximately 1.0–2.3 mm).
*Peduncle length.*—Medium (approximately 2.8–3.2 cm).
*Number of flowers.*—Many (approximately 14–16).
*Reproductive organs.*—1 pistil and 4 stamens.
*Flower fragrance.*—Absent.
*Flowering time.*—Late.
*Flowering duration.*—Long.

Physiological and ecological characteristics:
*Tolerance to cold.*—High.
*Tolerance to heat.*—High.
*Resistance to diseases.*—High.
*Resistance to pests.*—High.

This new 'Sunmariro' variety was propagated by the use of cuttings at Youkaichi-shi, Shiga-ken, Japan, and the homogeneity and stability thereof were confirmed. The new variety has been found to reproduce true to type in subsequent generations when asexually reproduced.

SUMMARY OF THE VARIETY

This new variety of Verbena plant has a spreading growth habit with medium stems, and a very broad spreading growth habit. The plant has much branching and a plentiful quantity of flowers in a spike with a great profusion of blooms. The blooming period is from early April to November, the flowers remain open in the rainy season and flowering duration is long. The entire plant remains in bloom for a considerable period of time. The flower size is large and the petal color of flowers is vivid red without the presence of an eye. The plant has high tolerance to cold and heat, high resistance to pests and diseases, particularly powdery mildew, and high resistance to rain.

It commonly takes approximately 12 weeks to produce a finished plant of the new variety following the rootings of a cutting.

BRIEF DESCRIPTION OF THE PHOTOGRAPHS

DESCRIPTION OF THE NEW VARIETY

Figure 1:
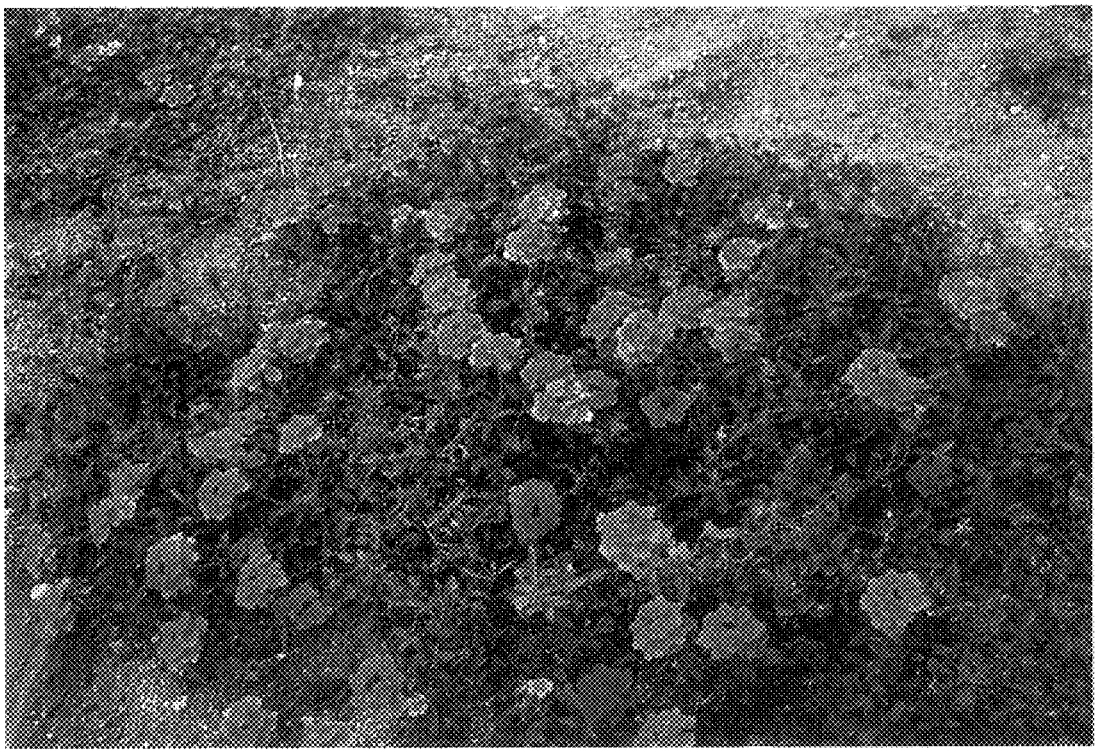
FIG. 1 is photograph showing a partial view of the new variety of Verbena plant while growing in the ground. Such plant was approximately four months of age.
Figure 2:
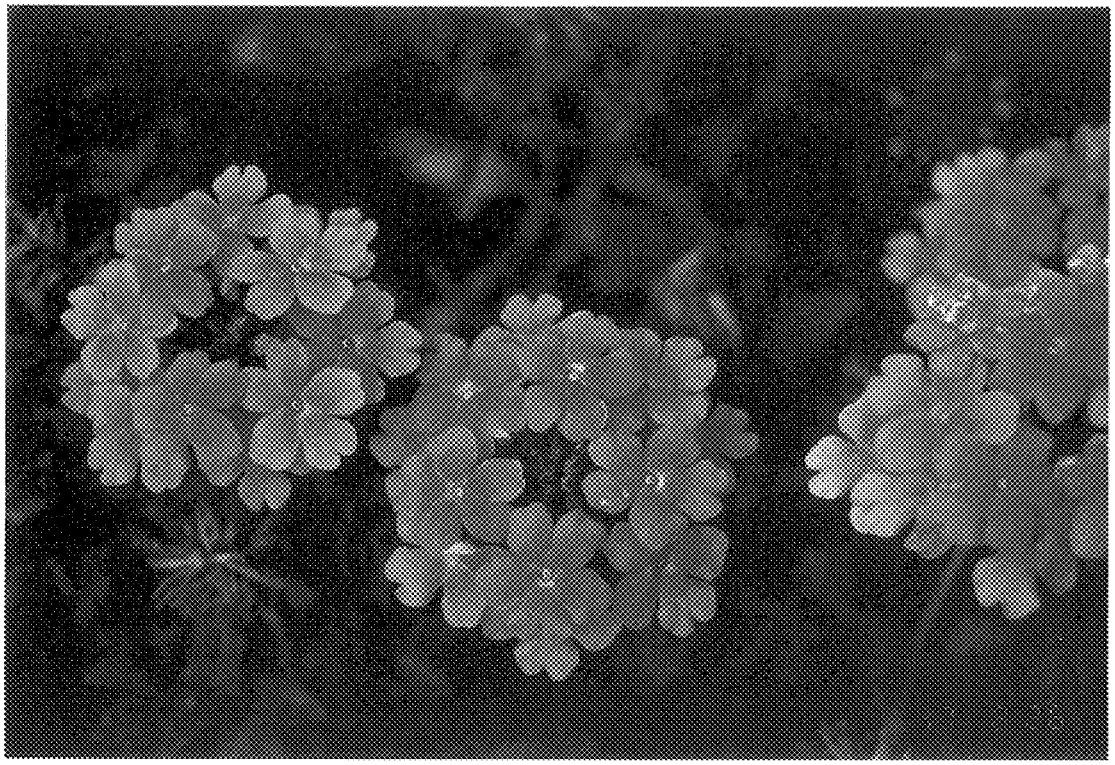
FIG. 2 is a photograph of flowers of the new variety of Verbena plant.

The botanical characteristics of the new and distinct variety of verbena plant named 'Sunmariro' are presented hereafter. The observed plants described herein were reproduced by the use of cuttings during May and were observed during the following August while growing in 10 to 12 inch pots at Hakushu-cho, Kitakoma-gun, Yamanashi-ken, Japan.

Plant:
*Growth habit.*—Spreading.
*Plant width.*—Broad (approximately 100–120 cm).
*Plant height.*—Medium (approximately 15–18 cm).

Stem:
*Diameter.*—Medium (approximately 1.5–2.5 mm).
*Length.*—Commonly approximately 2.5 to 5 cm.
*Anthocyanin pigmentation.*—Present (R.H.S. Colour Chart No. 59C).
*Pubescence.*—Medium.
*Prickles.*—Absent.
*Branching.*—Many.
*Subterranean stem.*—Absent.
*Length of internode.*—Medium (approximately 2.5–4.5 cm).

Leaf:
*Phyllotaxis.*—Opposite.
*Shape of blade.*—Hastate.
*Apex shape.*—Obtuse.
*Base shape.*—Truncate.
*Depth of blade incision.*—Shallow.
*Crenation of blade margin.*—Serrate.
*Length.*—Medium (approximately 2.5–3.2 cm).
*Width.*—Medium (approximately 1.4–2.2 cm).
*Color.*—Grayish olive green (R.H.S. Colour Chart No. 137A, J.H.S. Color Chart No. 3716) on the upper surface, and strong yellow green (R.H.S. Colour Chart No. 144A and J.H.S. Color Chart No. 3507) on the under surface.
*Venation pattern.*—Dichotomous.
*Pubescence.*—Sparse.
*Petiole.*—Present.
*Petiole diameter.*—Medium (approximately 1.0–1.2 mm).
*Petiole length.*—Short (approximately 1.5–2.5 mm).
*Petiole color.*—R.H.S. Colour Chart No. 137B.

Flower:
*Bud length.*—Approximately 1 to 1.5 cm.

*Bud diameter.*—Approximately 1.5 mm.
*Bud shape.*—Generally tubular.
*Bud color.*—R.H.S. Colour Chart No. 137C.
*Shape of cluster.*—Obconical.
*Cluster length.*—Medium (approximately 42–48 mm).
*Cluster diameter.*—Medium (approximately 53–60 mm).
*Facing direction.*—Upward.
*Outward curvature of petal.*—Slightly curved.
*Diameter.*—Large (approximately 18–22 mm).
*Length.*—Medium (approximately 1.7–2.0 cm).
*Color of petal.*—Substantially uniform vivid red (R.H.S. Colour Chart No. 57A, J.H.S. Color Chart No. 0107) on the upper surface, and strong pink (R.H.S. Colour Chart No. 58D, J.H.S. Color Chart No. 0104) on the under surface. The petal coloration fades slightly with age.
*Eye color.*—Absent.
*Variegation.*—Absent.
*Petal apex.*—Rounded.
*Petal shape.*—Tubular.
*Petal margin.*—Generally flat and uncurled.
*Incision of petal.*—Present in the apex of each petal.
*Number of petals.*—Medium (5).
*Calyx incision.*—Present at the apex.
*Calyx length.*—Long (approximately 1.0–1.2 cm).
*Calyx shape.*—Possesses one tubular sepal having an acute apex and a rounded base.
*Calyx color.*—R.H.S. Colour Chart No. 138A on the upper surface, and R.H.S. Colour Chart No. 138B on the under surface.
*Anthocyanin pigmentation of calyx limb.*—R.H.S. Colour Chart No. 60B.
*Pistil shape.*—Single and possesses two lobes.
*Stamen number.*—Commonly four.
*Anther color.*—Yellow green, R.H.S. Colour Chart No. 1B.
*Filament color.*—Yellow green, R.H.S. Colour Chart No. 1B.
*Pollen.*—Present in a moderate quantity, and R.H.S. Colour Chart No. 1B in coloration.
*Stigma color.*—R.H.S. Colour Chart No. 4D.
*Style color.*—R.H.S. Colour Chart No. 144B.
*Ovaries.*—Commonly four in number.
*Peduncle diameter.*—Thin (approximately 1.0–2.0 mm).
*Peduncle length.*—Medium (approximately 4.0–6.0 cm).
*Peduncle color.*—R.H.S. Colour Chart No. 137C.
*Number of flowers.*—Many (approximately 14–16).
*Reproductive organs.*—1 pistil and 4 stamens.
*Flower fragrance.*—Absent.
*Flowering time.*—Early.
*Flowering period.*—Long, and commonly begins in April and ends in about November.
*Flower longevity.*—An individual bloom commonly lasts approximately 5 to 7 days on the plant and varies with environmental conditions.

Physiological and ecological characteristics:
*Tolerance to cold.*—High.
*Tolerance to heat.*—High.
*Resistance to diseases.*—High.
*Resistance to pests.*—High.

This new variety of Verbena plant is most suitable for use in flower beds and for potting, particularly in hanging baskets and containers, and is further excellent for use as a ground cover. Pinching of old blossoms will enhance the formation of new blossoms.

I claim:

1. A new and distinct variety of Verbena plant, substantially as herein illustrated and described, characterized particularly as to novelty by (A) a spreading growth habit, (B) a plentiful number of flowers in a spike with a great profusion of blooms with the entire plant remaining in bloom for a considerable period of time, (C) a long flowering duration, (D) a large flower size and the petal color being vivid red without an eye, (E) a high resistance to rain, cold, heat, drought, diseases and pests, and (F) an early flowering time.

* * * * *